United States Patent
Bogdan et al.

(10) Patent No.: US 8,889,940 B2
(45) Date of Patent: Nov. 18, 2014

(54) CATALYST AND PROCESS FOR HYDROCARBON CONVERSION

(75) Inventors: Paula L. Bogdan, Mount Prospect, IL (US); Hui Wang, Des Plaines, IL (US); Richard R. Willis, Cary, IL (US)

(73) Assignee: UOP LLC, Des Plaines, IL (US)

( * ) Notice: Subject to any disclaimer, the term of this patent is extended or adjusted under 35 U.S.C. 154(b) by 160 days.

(21) Appl. No.: 13/286,553

(22) Filed: Nov. 1, 2011

(65) Prior Publication Data
US 2013/0109899 A1 May 2, 2013

(51) Int. Cl.
*C07C 15/08* (2006.01)
*B01J 29/40* (2006.01)
(Continued)

(52) U.S. Cl.
CPC ............ *B01J 29/06* (2013.01); *B01J 2229/186* (2013.01); *B01J 29/7492* (2013.01); *B01J 35/1042* (2013.01); *B01J 29/67* (2013.01); *B01J 29/126* (2013.01); *B01J 29/7484* (2013.01); *B01J 29/7469* (2013.01); *B01J 29/7446* (2013.01); *B01J 29/44* (2013.01); *B01J 29/7476* (2013.01); *B01J 35/002* (2013.01); *B01J 29/22* (2013.01); *B01J 37/16* (2013.01); *C07C 5/277* (2013.01); *C07C 2529/70* (2013.01); *B01J 35/08* (2013.01); *B01J 37/12* (2013.01); *B01J 29/74* (2013.01); *C07C 5/2732* (2013.01)
USPC ........... 585/481; 585/480; 585/482; 585/477; 585/475; 502/60; 502/63; 502/64; 502/66; 502/67; 502/71; 502/77; 502/78; 423/700; 423/709

(58) Field of Classification Search
CPC .......... C07C 2/66; C07C 5/27; C07C 5/2702; C07C 5/2708; C07C 5/2775; C07C 15/08; C07C 15/073; C07C 5/2737; B01J 35/10; B01J 35/1042; B01J 35/1047; B01J 35/002; B01J 35/0026; B01J 37/00; B01J 37/0072; B01J 37/06; B01J 29/00; B01J 29/06; B01J 29/40; B01J 29/7046; B01J 29/7042; B01J 29/7038; B01J 29/7034; B01J 29/7023
USPC .......................... 585/481, 475, 477, 480, 482; 423/700–718; 502/60, 63–71, 77, 78, 502/79
See application file for complete search history.

(56) References Cited

U.S. PATENT DOCUMENTS 3,909,450 A * 9/1975 O'Hara .......................... 502/200
4,864,068 A 9/1989 Shamshoum
(Continued)

FOREIGN PATENT DOCUMENTS

RU 2233260 C2 7/2004

OTHER PUBLICATIONS

International Search Report for PCT/US2012/056178, mailing date Mar. 6, 2013.

*Primary Examiner* — In Suk Bullock
*Assistant Examiner* — Philip Louie
(74) *Attorney, Agent, or Firm* — Mark R Willis

(57) ABSTRACT

The subject invention comprises a hydrocarbon-conversion process using a zeolitic catalyst comprising very low concentrations of non-zeolitic material and featuring a gradient in crystallinity decreasing from the outer portion to the center and an intrusion pore volume of at least 0.6 cc/gram. The catalyst is particularly effective in a xylene-isomerization process comprising ethylbenzene conversion.

7 Claims, 1 Drawing Sheet

(51) Int. Cl.
*B01J 35/10* (2006.01)
*B01J 29/44* (2006.01)
*B01J 35/00* (2006.01)
*B01J 37/16* (2006.01)
*C07C 5/27* (2006.01)
*B01J 35/08* (2006.01)
*B01J 37/12* (2006.01)
*B01J 29/06* (2006.01)
*B01J 29/74* (2006.01)
*B01J 29/67* (2006.01)
*B01J 29/12* (2006.01)
*B01J 29/22* (2006.01)

(56) References Cited

U.S. PATENT DOCUMENTS

| | | |
|---|---|---|
| 5,665,325 A | 9/1997 | Verduijn |
| 6,039,864 A | 3/2000 | Mohr |
| 7,026,264 B2 | 4/2006 | Mohr et al. |
| 7,297,830 B2 | 11/2007 | Bogdan et al. |
| 7,807,045 B2 | 10/2010 | Rende et al. |
| 7,812,205 B2 | 10/2010 | Jan et al. |
| 2001/0002426 A1* | 5/2001 | Mohr et al. .................. 585/407 |
| 2007/0060778 A1* | 3/2007 | Bogdan et al. ............... 585/481 |
| 2009/0023968 A1 | 1/2009 | Wang et al. |
| 2011/0245565 A1 | 10/2011 | Bogdan et al. |
| 2013/0064757 A1* | 3/2013 | Jan et al. ...................... 423/703 |

\* cited by examiner

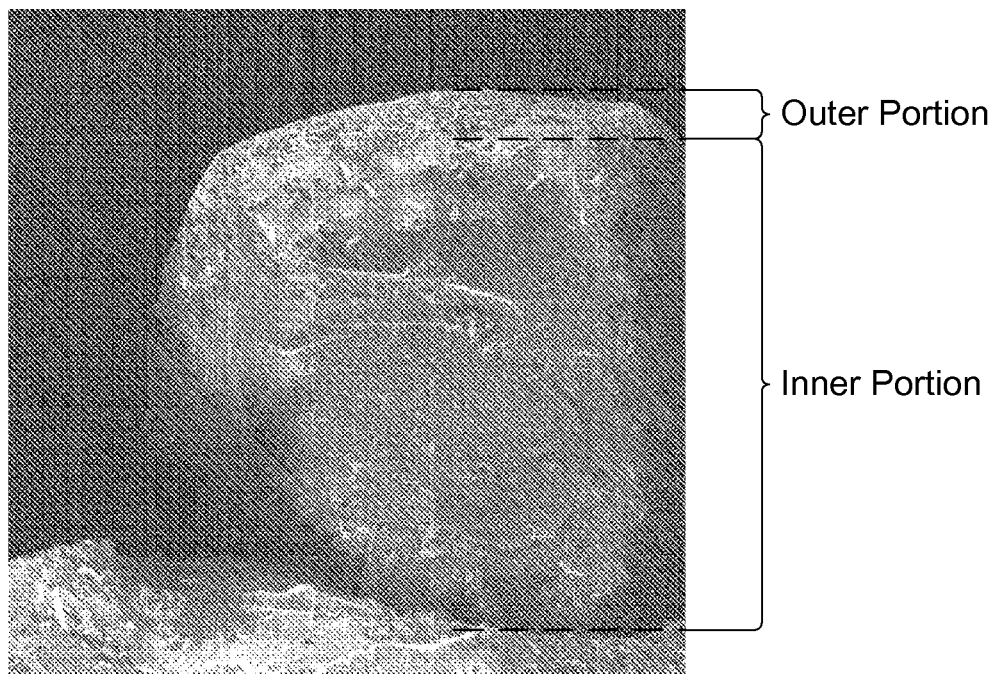

CATALYST AND PROCESS FOR HYDROCARBON CONVERSION

FIELD OF THE INVENTION

This invention relates to catalysts and processes for hydrocarbon conversion. More specifically, the invention discloses catalysts for the efficient conversion of ethylbenzene and isomerization of xylenes.

BACKGROUND OF THE INVENTION

Zeolites are widely used as catalysts for various types of hydrocarbon-conversion processes such as isomerization, reforming, hydrogenation, alkylation, transalkylation, cracking and hydrocracking. In addition, zeolitic materials are used as adsorbents in various petroleum and chemical separation processes. Selectivity in catalysis or separation is conferred by the interstitial spaces or channels formed by the network of crystalline aluminosilicates. Zeolites also may comprise materials in which the silica and alumina portions have been replaced in whole or in part with other oxides; germanium oxide, tin oxide, and mixtures thereof can replace the silica portion and gallium oxide, indium oxide, boron oxide, iron oxide, and mixtures thereof can replace the alumina portion.

The practical applications of pure zeolites are severely limited because of mechanical-strength limitations. Mechanical strength may be conferred by forming the zeolite in the presence of a non-zeolitic binder and drying and calcining the resulting extrudate pill, sphere, or extrudate. Examples of such binders include materials such as alumina, silica, titanium, and various types of clays. However, the effectiveness of a bound zeolite in terms of activity, selectivity, or activity maintenance, can be reduced because the binder dilutes the adsorptive properties of the zeolite. In addition, since the bound zeolite is prepared by extruding the zeolite with the binder and subsequently drying and calcining the extrudate, the amorphous binder can penetrate the pores of the zeolite, otherwise block access to the pores of the zeolite, or slow the rate of mass transfer to the pores of the zeolite which can reduce the effectiveness of the zeolite. Still further, when a bound zeolite is used in catalytic processes, the binder may affect the chemical reactions that are taking place within the zeolite and also may catalyze undesirable reactions which can result in the formation of undesirable products.

A key application of zeolitic catalysts is in the conversion of $C_8$ aromatics to obtain individual xylene isomers. The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production.

The catalytic reforming of petroleum naphtha is an important source of $C_8$ aromatics. Xylene isomers in $C_8$ aromatics from catalytic reforming or other sources generally do not match demand proportions as chemical intermediates, and further comprise ethylbenzene which is difficult to separate or to convert. Para-xylene in particular is a major chemical intermediate with rapidly growing demand, but amounts to only 15-20% of a typical $C_8$-aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture which approaches equilibrium concentrations. The approach to equilibrium that is used is an optimized compromise between high $C_8$ cyclic loss at high conversion (i.e. very close approach to equilibrium) and high utility costs due to the large recycle rate of unconverted $C_8$ aromatics.

Processes for conversion of $C_8$ aromatics ordinarily are classified by the manner of converting ethylbenzene associated with the xylene isomers. Ethylbenzene is not easily isomerized to xylenes, but it normally is converted in the process unit because separation from the xylenes by superfractionation or adsorption is very expensive. One approach is to react the ethylbenzene to form a xylene mixture via conversion to and reconversion from naphthenes in the presence of a solid acid catalyst with a hydrogenation-dehydrogenation function. An alternative widely used approach is to dealkylate ethylbenzene to form principally benzene while isomerizing xylenes to a near-equilibrium mixture. The former approach enhances xylene yield by forming xylenes from ethylbenzene; the latter approach commonly results in higher ethylbenzene conversion, thus lowering the quantity of recycle to the para-xylene recovery unit and concomitant processing costs.

Hydrogen generally is present in the conversion process reactants to aid in the reaction and maintain catalyst stability. Although xylenes may be isomerized in the absence of hydrogen under some circumstances with resulting cost savings, ethylbenzene conversion generally requires the presence of hydrogen. Two-stage processing units may be justified in some cases to obtain both high conversion and ethylbenzene yield. In any case, the search continues for more effective catalysts and processes.

SUMMARY OF THE INVENTION

A principal object of the present invention is to provide a novel catalyst effective for the conversion of hydrocarbons. More specifically, the invention comprises a process for the conversion of alkylaromatic hydrocarbons and particularly for the processing of $C_8$ aromatics to increase the concentration of a desired xylene isomer with reduced aromatic losses and lowered processing costs.

This invention is based on the discovery that conversion of ethylbenzene in connection with xylene isomerization can be effected with a catalyst comprising a binderless zeolite having specific characteristics of porosity and crystallinity gradient.

Accordingly, one embodiment of the invention is a process for the conversion of a non-equilibrium $C_8$-aromatic feedstock comprising contacting the feedstock with a catalyst bed, comprising particles of an unbound zeolitic aluminosilicate having an particle intrusion pore volume of at least 0.65 cc/gram and a particle crystallinity gradient increasing in the proportion of crystallinity from a low-crystallinity inner portion to a high-crystallinity outer portion, in a conversion zone at conversion conditions comprising a temperature of from about 340° C. to 500° C., a pressure of from 100 kPa to 5 MPa, and a mass hourly space velocity of from about 2 to 50 $hr^{-1}$ in the presence of hydrogen to convert ethylbenzene and obtain an isomerized product comprising a higher proportion of at least one xylene isomer than in the feedstock.

A more specific embodiment is a process for the conversion of a non-equilibrium $C_8$-aromatic feedstock comprising contacting the feedstock with a catalyst bed, comprising particles of an unbound zeolitic aluminosilicate having an particle intrusion pore volume of at least 0.65 cc/gram and a particle crystallinity gradient increasing in the proportion of crystallinity from an inner portion having relative crystallinity from about 10 to about 50 weight percent to a high-crystallinity 500-micron outer portion having relative crystallinity from about 90 to about 100 weight percent, in a conversion zone at conversion conditions comprising a temperature of from about 340° C. to 500° C., a pressure of from 100 kPa to 5 MPa, and a mass hourly space velocity of from about 2 to 50 $hr^{-1}$ in the presence of hydrogen to convert ethylbenzene and obtain an isomerized product comprising a higher proportion of at least one xylene isomer than in the feedstock.

A yet more specific embodiment is a process for the conversion of a non-equilibrium $C_8$-aromatic feedstock comprising contacting the feedstock with a catalyst bed, comprising particles of an unbound zeolitic aluminosilicate having an particle intrusion pore volume of at least 0.65 cc/gram and a particle crystallinity gradient increasing in the proportion of crystallinity from an inner portion having relative crystallinity from about 10 to about 50 weight percent to a high-crystallinity 100-micron outer portion having relative crystallinity from about 90 to about 100 weight percent, in a conversion zone at conversion conditions comprising a temperature of from about 340° C. to 500° C., a pressure of from 100 kPa to 5 MPa, and a mass hourly space velocity of from about 2 to 50 $hr^{-1}$ in the presence of hydrogen to convert ethylbenzene with a xylene loss of less than about 0.02 per % ethylbenzene conversion and obtain an isomerized product comprising a higher proportion of at least one xylene isomer than in the feedstock.

Other specific embodiments will become clear from the following detailed description of the invention.

BRIEF DESCRIPTION OF THE ILLUSTRATION

FIG. 1 shows characteristics of a particle of the invention.

DETAILED DESCRIPTION OF THE INVENTION

Binderless spherical zeolitic particles of the invention feature high catalytic activity and selectivity for the conversion of hydrocarbons and especially for the conversion of aromatic hydrocarbons. Examples of zeolites comprising catalysts of the invention include those having Si:$Al_2$ ratios greater than about 10, and often greater than about 20, such as the MFI, MEL, EUO, FER, MFS, MTT, MTW, TON, MOR and FAU types of zeolites as framework type as described in *Atlas of Zeolite Framework Types,* 6th Revised Edition, C. H. Baerlocher, L. B. McCusker, and D. H. Olson, editors, Elsevier (2007). Pentasil zeolites such as MFI, MEL, MTW and TON are preferred, and MFI-type zeolites, such as ZSM-5, silicalite, Borolite C, TS-1, ZSM-12, SSZ-25, PSH-3, and ITQ-1 are especially preferred.

Preparing the preferred catalyst of the invention first comprises forming a reaction mixture of aluminum and silicon. The sources of aluminum include but are not limited to aluminum alkoxides, precipitated aluminas, aluminum metal, aluminum salts and alumina sols. Specific examples of aluminum alkoxides include, but are not limited to aluminum sec-butoxide and aluminum ortho isopropoxide. Sources of silica include but are not limited to tetraethylorthosilicate, colloidal silica, precipitated silica, alkali silicates, HiSil and Ultrasil. The ratio Si/Al may range from about 3 to about 100, and preferably from about 8 to about 50.

The silica-alumina mixture preferably contains substantially no zeolite, as described hereinabove, or structure-directing agent, as described herein below, although it is within the scope of the invention that relatively small amounts of such materials are present.

A preferred method comprises preparation of an amorphous silica-alumina by means well known in the art. For example, the procedure set forth in U.S. Pat. No. 3,909,450, which is incorporated by reference, may be used. This procedure involves making an aluminum sol by digesting aluminum in an aqueous hydrochloric acid solution at reflux temperature to form a sol with a predetermined aluminum/chloride ratio. This aluminum sol is mixed with a silicon sol which has been prepared, for example, by the acidification of water glass. Gelling agents such as hexamethylenetetraamine, urea or mixtures thereof are added and the sol mixture dispersed as droplets in a hot oil bath where gelation occurs with the formation of spheroidal particles. The gelling agent increases the pH of the sol droplets, causing the droplets to gel. This sol-gel process sets the alumina and silica. Further details regarding the oil drop method may be found in U.S. Pat. No. 2,620,314 which is incorporated by reference.

Although the above procedure provides an amorphous silica-alumina composition in the form of spheres, the amorphous silica-alumina may be in any form such as extrudate, irregularly shaped particles, pills or tablets as long as these correspond respectively to the form of the finished catalyst. It is especially preferred to use spheres prepared as described above.

The spheres are continuously withdrawn from the oil bath and typically subjected to specific aging and drying treatment in oil and an aqueous ammonia solution to effect the catalyst of the invention. The resulting aged and gelled particles are then washed and dried at a relatively low temperature of about 90° C. to about 150° C. and subjected to a calcination procedure at a temperature of about 400° C. to about 700° C. for a period of about 1 to about 20 hours. This provides an amorphous silica-alumina composition. These amorphous silica-alumina compositions are characterized in that they have an apparent bulk density of about 0.3 to about 0.5 g/cc and a pore volume of about 0.4 to about 1.0 cc/g.

The catalyst preferably is binderless, i.e., comprises a form suitable for a hydrocarbon-conversion process without the substantial presence of inert components enabling the shape of the finished catalyst. If present, such components are present in a minor amount, e.g., less than about 50 mass-%, preferably less than about 10 mass-%, and most preferably less than about 7 mass-% based upon the mass of the catalyst. Any inert components preferably comprise unconverted material from crystallization of a preformed sphere.

Binderless catalysts are prepared from extrudates or spherical particles composed of, for example, amorphous or crystalline silica and alumina or amorphous silica alumina oxide sources. A mineralizing agent, such as an amine, sodium hydroxide and/or sodium fluoride, tetraalkyl ammonium hydroxide or bromide, the alkyl groups preferably containing 2-5 carbon atoms, and water are also required in order to convert the silica and alumina components into binderless aluminosilicate zeolite particles. The mineralizing agent and water may be incorporated into the spherical particles or extrudates during the forming process, or they can be added later either as a solution, multiple solutions, steam, vapor or any combination thereof. Seeds, nucleating agents, and/or structure directing agents can also be added in small quantities, but in general these are not necessary and/or their use can be avoided. The resulting product may then be optionally calcined in air at temperatures of 400-550° C. for a period of 10-40 hours to remove tetraalkylammonium cations.

The product can be further treated in order to remove aluminum and optionally inserting silicon thereby increasing the Si/Al ratio and thus modifying the acidity and ion exchange properties of the zeolites. These treatments include: a) contacting with a fluorosilicate solution or slurry; b) calcining or steaming followed by acid extraction or ion-exchange; c) acid extraction or d) any combination of these treatments in any order.

Catalysts of the invention feature exceptionally high macroporosity and high intrusion volumes, measured in accordance with ASTM D4284 Standard Test Method for Determining Pore Volume Distribution of Catalyst by Mercury Intrusion Porosimetry corresponding to intrusion of a volume of mercury which is characteristic of the existence of mesopores and macropores into the catalyst. The particle intrusion pore volume generally is at least 0.60 cc/gram, preferably at least 0.65 cc/gram, and more preferably greater than 0.70 cc/gram. These characteristics lead to high conversion of ethylbenzene in a $C_8$-aromatics mixture compared to catalysts prepared by binding a zeolite.

A gradient of crystallinity preferably is determined by Scanning Electron Microscopy ("SEM"). SEM determinations of local crystallinity are effected on at least three sample particles from a bed of catalyst particles. Samples are selected from the bed by techniques known to those of ordinary skill in the art. The SEM data show the approximate crystallinity of any one point within a catalyst particle, based on the crystallinity in relation to the position relative to the diameter of the particle. Measurement of the gradient is effected as the average of the gradient at given levels in at least three catalyst particles, and are useful for making relative comparisons of crystallinity. The particle crystallinity gradient increases in the proportion of crystallinity from a low-crystallinity inner portion having crystallinity from about 10 to about 50 weight percent to a high-crystallinity outer portion having a crystallinity from about 90 to about 100 weight percent; the inner portion may comprise about 50% of the volume of the particle. This gradient contrasts with a catalyst having a outer layer of zeolite over an amorphous center.

FIG. 1 illustrates a particle of the invention which has been sliced to demonstrate the gradient of the invention. The outer portion of the particle shows a high degree of crystallinity, while the central portion shows only a few crystals. The proportion of crystals increases as observations move toward the outer portion.

Catalysts of the invention preferably contain a metal component, comprising one or more metals selected from Group VIII (IUPAC 8-10), Group VIB (IUPAC 6), and Group VIIB (IUPAC 7) metals. One or more of the platinum-group metals, including one or more of platinum, palladium, rhodium, ruthenium, osmium, and iridium, are particularly favored components of the present catalyst. The preferred platinum-group metals are platinum and palladium, with platinum being especially preferred. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all of the platinum-group metal component exists in a reduced state. The platinum-group metal component generally comprises from about 10 to about 5000 mass-ppm (parts per million) of the final catalyst composite, calculated on an elemental basis, with a level of about 100 to about 2000 mass-ppm being particularly suitable. When using a platinum component, levels of about 200 to 800 mass-ppm of platinum on the catalyst on an elemental basis are favored; and levels of about 200 to about 500 mass-ppm are especially favored.

The hydrogenation metal component may be incorporated into the catalyst composite in any suitable manner. One method of preparing the catalyst involves the utilization of a water-soluble, decomposable compound of the hydrogenation metal to impregnate the calcined sieve/binder composite.

It is within the scope of the present invention that the catalyst composites may contain, in addition, metal modifiers such as one or more of rhenium, tin, germanium, lead, cobalt, nickel, indium, gallium, zinc, uranium, dysprosium, thallium, and mixtures thereof. Catalytically effective amounts of such metal modifiers may be incorporated into the catalysts by any means known in the art to effect a homogeneous or stratified distribution.

In an alternative embodiment, the catalyst may comprise a dispersed, selectively sulfided rhenium component. The rhenium (calculated as the elemental metal) is present in an amount of between about 0.05 and 5, preferably 0.4 to 4, mass of the catalyst and the atomic ratio of sulfur to rhenium is between about 0.2:1 to 0.7:1, preferably 0.25:1 to 0.5:1. The first sulfiding of the alternative catalyst preferably employs a highly dilute sulfiding gas under sulfiding conditions, passing the sulfur-containing gas over the catalyst, e.g., at a weight hourly space velocity of at least about 0.5 hr$^{-1}$ and a temperature of at least about 100° C. as known in the art. Reducing conditions may be provided by the presence of at least one of hydrocarbon and hydrogen in the substantial absence of an oxidizing component. The sulfiding gas frequently contains less than about 5000, more preferably less than about 500, parts per million by mole (ppm-mole) sulfur.

The catalysts of the present invention may contain a halogen component, comprising fluorine, chlorine, bromine or iodine or mixtures thereof, with chlorine being preferred. Preferably, however, the catalyst contains no added halogen other than that associated with other catalyst components.

The catalyst composite is dried, preferably at a temperature of from about 100° to about 320° C. for a period of from about 2 to about 24 or more hours. If desired, the catalyst may be calcined at a temperature of from about 400° to about 650° C. in an air atmosphere for a period of from about 0.1 to about 10 hours. Steam may also be present during the calcination, e.g., from about 0.5 to 20, say, about 1 to 10, mol-% steam based on the air. Where the catalyst contains a minor amount of platinum group metal, the resultant calcined composites often are subjected to a substantially water-free reduction step to ensure a uniform and finely divided dispersion of the optional metallic components. The reducing agent contacts the catalyst at conditions, including a temperature of from about 200° to about 650° C. and for a period of from about 0.5 to about 10 hours, effective to reduce substantially all of the platinum group metal component, if present, to the metallic state.

Efficient conversion of ethylbenzene in a $C_8$-aromatic mixture in combination with isomerization of xylenes is a particularly preferred application of the present catalyst. Feedstocks to the preferred aromatics-conversion process comprise non-equilibrium xylene and ethylbenzene. These aromatic compounds are in a non-equilibrium mixture, i.e., at least one $C_8$-aromatic isomer is present in a concentration that differs substantially from the equilibrium concentration at isomerization conditions. Thus, a non-equilibrium xylene composition exists where one or two of the xylene isomers are in less than equilibrium proportion with respect to the other xylene isomer or isomers. The xylene in less than equilibrium proportion may be any of the para-, meta- and ortho-isomers. As the demand for para- and ortho-xylenes is greater than that for meta-xylene, usually, the feedstocks will contain meta-xylene. Generally the mixture will have an ethylbenzene content of about 1 to about 60 mass-%, an ortho-xylene content of 0 to about 35 mass-%, a meta-xylene content of about 20 to about 95 mass-% and a para-xylene content of 0 to about 30 mass-%. Usually, the non-equilibrium mixture is prepared by removal of para-, ortho- and/or meta-xylene from a fresh $C_8$ aromatic mixture obtained from an aromatics-production process. The feedstocks may contain other components, including, but not limited to naphthenes and acyclic paraffins, as well as higher and lower molecular weight aromatics.

The alkylaromatic hydrocarbons may be used in the present invention as found in appropriate fractions from various refinery petroleum streams, e.g., as individual components or as certain boiling-range fractions obtained by the selective fractionation and distillation of catalytically cracked or reformed hydrocarbons.

According to the process of the present invention, the alkylaromatic hydrocarbon feed mixture, preferably in admixture with hydrogen, is contacted with a catalyst of the invention in an alkylaromatic hydrocarbon conversion zone. Contacting may be effected using the catalyst in a fixed-bed system, a moving-bed system, a fluidized-bed system, or in a batch-type operation. In view of the danger of attrition loss of the valuable catalyst and of the simpler operation, it is preferred to use a fixed-bed system. In this system, a hydrogen-rich gas and the feed mixture are preheated by suitable heating means to the desired reaction temperature and then passed into a conversion zone containing a fixed bed of catalyst. The conversion may be effected in one or more separate reactors with suitable means therebetween to ensure that the desired conversion temperature is maintained at the entrance to each zone.

The reactants may be contacted with a catalyst bed in either upward-, downward-, or radial-flow fashion, and the reactants may be in the liquid phase, a mixed liquid-vapor phase, or a vapor phase when contacted with the catalyst. The reactants preferably are partially or wholly in the vapor phase.

The alkylaromatic feed mixture, preferably a non-equilibrium mixture of $C_8$ aromatics, is contacted with the conversion catalyst at suitable alkylaromatic-conversion conditions. Such conditions comprise a temperature ranging from about 100° to 600° C. or more, and preferably is in the range of from about 340° to 500° C. The pressure generally is from about 100 kPa to 10 MPa, and more usually no more than about 5 MPa. Sufficient catalyst is contained in the conversion zone to provide a mass hourly space velocity with respect to the hydrocarbon feed mixture of from about 0.5 to 100 $hr^{-1}$, and preferably 2 to 50 $hr^{-1}$; favorable results have been obtained at mass hourly space velocities of at least about 10 $hr^{-1}$ and higher. The hydrocarbon feed mixture optimally is reacted in admixture with hydrogen at a hydrogen/hydrocarbon mole ratio of about 0.05:1 to about 10:1 or more, and preferably at least 0.05; inert diluents such as nitrogen, argon and light hydrocarbons also may be present.

Usually the conversion conditions are sufficient to convert at least about 50, preferably between about 60 and 90, percent of the ethylbenzene in the feed stream. The present process features a high degree of removal of the ethyl radical from ethylbenzene with low formation of toluene and heavy alkylbenzene byproducts. Generally the conversion conditions do not result in a xylene equilibrium being reached. The conversion process generally converts ethylbenzene with a % xylene loss of less than about 0.025, and preferably less than about 0.02, per % ethylbenzene conversion.

It is within the invention that an alkylaromatic hydrocarbon feed mixture is contacted sequentially with two or more catalysts in a conversion zone followed by a subsequent xylene-isomerization zone to achieve the objectives of the invention. Such a two-catalyst system is particularly effective through efficient ethylbenzene conversion followed by effective xylene isomerization in a low-ethylbenzene $C_8$-aromatics mixture. Contacting may be effected in either zone using the catalyst system in a fixed-bed system, a moving-bed system, a fluidized-bed system, slurry system, an ebullated-bed system or in a batch-type operation, but it is preferred to use a fixed-bed system in both zones. The first conversion zone preferably contains a catalyst of the invention operating at conditions effective to convert ethylbenzene as well as to isomerize xylenes as described hereinabove. The first conversion zone yields an intermediate stream, and at least part of and preferably the entire intermediate stream without further processing is contacted in a second conversion zone containing an isomerization catalyst. The isomerization zone may comprise a single reactor or two or more separate reactors with suitable means therebetween to achieve an improved approach to xylene equilibrium. The two catalysts preferably are contained within the same reactor.

The isomerization zone preferably contains a catalyst particularly effective for xylene isomerization, ethylbenzene having been converted in the first zone. Any catalyst effective for this purpose may be used, including known zeolitic aluminosilicates selected from MFI, MEL, EUO, FER, MFS, MTT, MTW, TON, MOR and FAU types with pentasil zeolites MFI and MTW being preferred. The reactants may contact the second catalyst in liquid phase, a mixed liquid-vapor phase, or a vapor phase. Operating conditions generally are within the range described above for the catalyst of the invention, with a lower temperature in the range of 200° to 400° C. being preferred to achieve para-xylene ratios in the upper range described hereinabove.

The particular scheme employed to recover an isomerized product from the effluent of the reactors is not deemed to be critical to the instant invention, and any effective recovery scheme known in the art may be used. Typically, the conversion product is fractionated to remove light by-products such as alkanes, naphthenes, benzene and toluene, and heavy byproducts to obtain a $C_8$ isomer product. Heavy byproducts include dimethylethylbenzene and trimethylbenzene. In some instances, certain product species such as ortho-xylene or dimethylethylbenzene may be recovered from the isomerized product by selective fractionation. The product from conversion of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. Nos. 3,626,020, 3,696,107, 4,039,599, 4,184,943, 4,381,419 and 4,402,832, incorporated herein by reference.

EXAMPLES

The following examples are presented only to illustrate certain specific embodiments of the invention, and should not be construed to limit the scope of the invention as set forth in the claims. There are many possible other variations, as those of ordinary skill in the art will recognize, within the spirit of the invention.

Example 1

A first catalyst of the invention was prepared as follows: into a 125 mL Teflon liner, 11.8 grams of propylamine and 4.0 grams of 10% NaCl aqueous solution were mixed. To that mixture, 8.0 grams of calcined oil-dropped spheres with Si/Al$_2$ ratio of 80 were added and totally covered by the liquid phase. The Teflon liner was then loaded into a Parr reactor and heated to 175° C. for 10 days. After being cooled to room temperature, the spheres were filtered and washed with deionized water. The calcined particles of catalyst contained 70% MFI by x-ray diffraction. The catalyst was finished by impregnating 111 grams of the calcined product with a 200 milliliters aqueous solution containing 0.08 grams of tetraamineplatinum chloride and 9.41 grams of NH$_4$NO$_3$ followed by evaporation at 100° C. to yield a final platinum level of 0.04 mass percent on the finished catalyst particles. The impregnated samples then were subjected, as described in Example 1 of U.S. Pat. No. 7,939,701, to a two-stage calcination and an 88° C. ammonium ion exchange followed by a 480° C. oxidation and a 4-hour 425° C. reduction. The catalyst had an ASTM D4284 intrusion volume of 0.718 cc/gram and a platinum content of 220 ppm and is designated as Catalyst A.

Example 2

A second catalyst of the invention was prepared as follows: into a 125 mL Teflon liner, 15 grams of butylamine and 10 grams of 20% NaCl aqueous solution were mixed. To that mixture, 12 grams of calcined oil-dropped spheres with Si/Al2 of 40 were added and totally covered by the liquid phase. The Teflon liner was then loaded into a Parr reactor and heated to 175° C. for 10 days. After being cooled to room temperature, the spheres were filtered and washed with DI water. The calcined particles of catalyst contained 50% MFI by x-ray diffraction. The catalyst was finished by impregnating 111 grams of the calcined product with a 200 milliliters aqueous solution containing 0.08 grams of tetraamineplatinum chloride and 9.41 grams of NH$_4$NO$_3$ followed by evaporation at 100° C. to yield a final platinum level of 0.04 mass percent on the finished catalyst particles. The impregnated samples then were subjected, as described in Example 1 of U.S. Pat. No. 7,939,701, to a two-stage calcination and an 88° C. ammonium ion exchange followed by a 480° C. oxidation and a 4-hour 425° C. reduction. The catalyst had an ASTM D4284 intrusion volume of 0.743 cc/gram and a platinum content of 350 ppm and is designated as Catalyst B.

Example 3

Performance of catalysts of the invention was compared to a reference catalyst of the known art prepared according to Example 2 of U.S. Pat. No. 7,939,701. The tests each were affected by isomerizing a feed stream having the substantial absence of para-xylene and containing 15 mass-percent ethylbenzene, 25 mass-percent ortho-xylene and 60 mass-percent meta-xylene. The tests were conducted at a hydrogen to hydrocarbon ratio of 4 to 1, a weight hourly space velocity of 7 and pressure of 0.7 MPa gauge. Ethylbenzene conversion of 70% was effected at test temperatures ranging from 375 to 400° C. Performance was measured as the loss of xylenes and concomitant yield of byproduct toluene and heavy alkylbenzene as follows:

| Catalyst | A | B | Reference |
|---|---|---|---|
| Temperature, ° C. | 375 | 388 | 371 |
| Para-xylene/xylenes, % | 16 | 6 | 24 |
| Xylene loss, % | 1.1 | 0.4 | 1.9 |
| Toluene + heavy byproduct, mass-% | 0.9 | 0.3 | 1.7 |

Both catalysts of the invention demonstrate lower xylene loss and byproduct yield than the reference catalyst while converting ethylbenzene and increasing the proportion of para-xylene in the product. Note that the ratios of xylene loss to ethylbenzene conversion were, respectively, 0.016, 0.006, and 0.027.

The invention claimed is:

1. A process for the conversion of a non-equilibrium C$_8$-aromatic feedstock comprising contacting the feedstock with a catalyst bed, comprising particles of an unbound zeolitic aluminosilicate comprising an MFI zeolite and one or more metals selected from Groups VIII, Group VIB, and Group VIIB, having a particle intrusion pore volume of at least 0.65 cc/gram and a particle crystallinity gradient increasing in the proportion of crystallinity from an inner portion having a relative crystallinity from about 10 to about 50 weight percent to a high-crystallinity outer portion having a relative crystallinity from about 90 to about 100 weight percent, in a conversion zone at isomerization conditions comprising a temperature of from about 340° C. to 500° C., a pressure of from 100 kPa to 5 MPa, and a mass hourly space velocity of from about 2 to 50 hr$^1$ in the presence of hydrogen to convert ethylbenzene with low xylene loss and obtain an isomerized product comprising a higher proportion of at least one xylene isomer than in the feedstock.

2. The process of claim 1 wherein the particle intrusion pore volume is at least about 0.7 cc/gram.

3. The process of claim 1 wherein the inner portion of the catalyst particle is defined as the inner 50% of the volume of the particle.

4. The process of claim 1 wherein the catalyst has a spherical configuration.

5. The process of claim 4 wherein the spherical configuration of the catalyst comprises characteristics of oil dropping.

6. The process of claim 1 wherein the xylene loss is less than about 0.02% per % ethylbenzene conversion.

7. The process of claim 1 further comprising a subsequent xylene-isomerization zone.

\* \* \* \* \*